United States Patent [19]

Clift, Jr. et al.

[11] Patent Number: 5,431,656
[45] Date of Patent: Jul. 11, 1995

[54] INTRAMEDULLARY INSTRUMENTATION TO POSITION MEANS FOR PREPARING A TIBIAL PLATEAU WITH A POSTERIOR SLOPE

[75] Inventors: Joseph S. Clift, Jr.; James E. Van Hoeck, both of Memphis, Tenn.; Leo A. Whiteside, Chesterfield, Mo.

[73] Assignee: Wright Medical Technology, Inc., Arlington, Tenn.

[21] Appl. No.: 188,578

[22] Filed: Feb. 4, 1994

[51] Int. Cl.6 .............................................. A61B 17/00
[52] U.S. Cl. ...................................... 606/86; 606/87
[58] Field of Search .................. 606/86, 88, 89, 87, 606/79, 80, 81, 84, 85, 96, 98

[56] References Cited

U.S. PATENT DOCUMENTS 4,211,228  7/1980  Cloutier ........................ 606/88 X
4,467,801  8/1984  Whiteside .
4,913,137  4/1990  Azer et al. .................... 606/96 X
5,002,545  3/1991  Whiteside et al. ............. 606/80
5,037,423  8/1991  Kenna ........................... 606/87 X
5,282,803  2/1994  Lackey ........................... 606/96 X Primary Examiner—Peter A. Aschenbrenner
Attorney, Agent, or Firm—Walker, McKenzie & Walker

[57] ABSTRACT

Instrumentation for positioning a cut guide to cut a posterior slope in the tibial plateau surface of a tibia. The instrumentation includes an intramedullary alignment guide for engaging the tibia, and a rotational alignment guide for providing a guide for the insertion of a rod portion of the intramedullary alignment guide into an intramedullary bore in the tibia with the intramedullary alignment guide rotationally aligned with the intramedullary bore so that the longitudinal axis of a handle portion of the intramedullary alignment guide is angled posteriorly with respect to the longitudinal axis of the rod portion and the longitudinal axis of the intramedullary bore as the rod portion of the intramedullary alignment guide is inserted into the intramedullary bore.

2 Claims, 3 Drawing Sheets

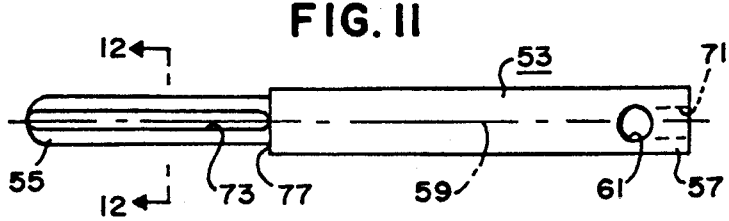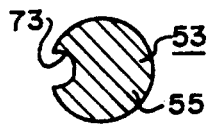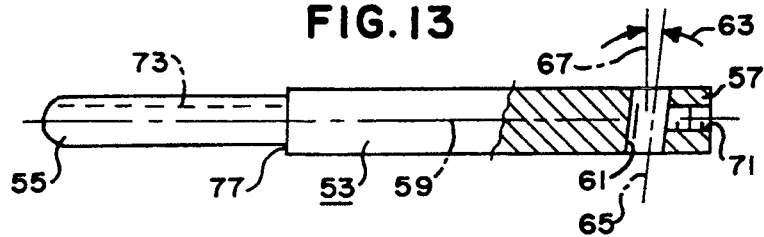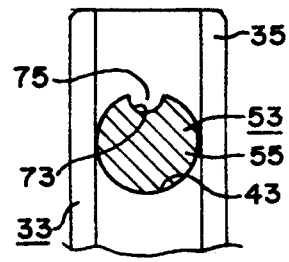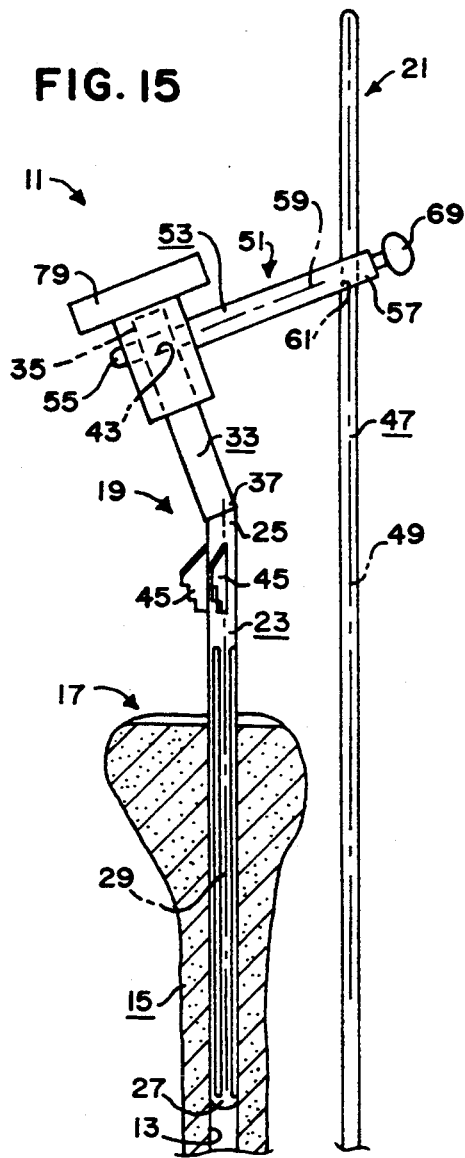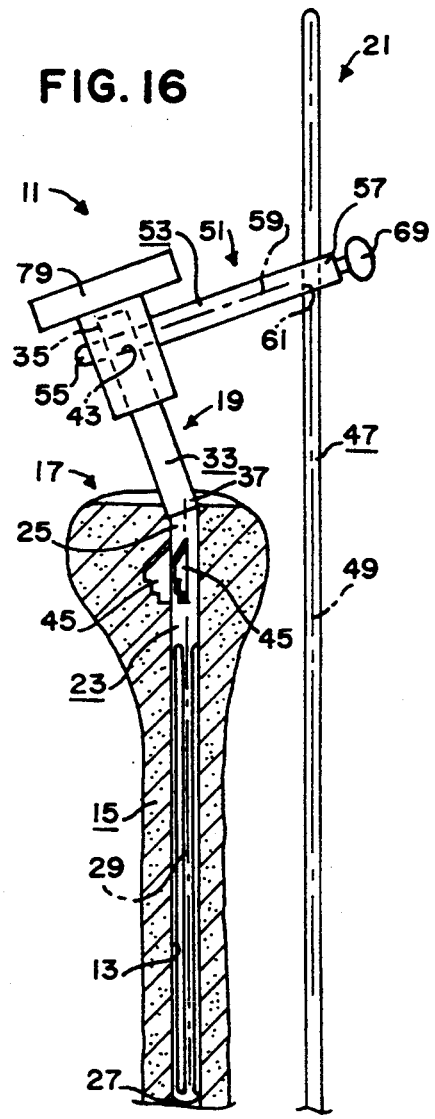

INTRAMEDULLARY INSTRUMENTATION TO POSITION MEANS FOR PREPARING A TIBIAL PLATEAU WITH A POSTERIOR SLOPE

BACKGROUND OF THE INVENTION

1. Field of the Invention

The present invention relates to instrumentation using the medullary canal of a tibia to accurately position means for preparing a tibial plateau with a posterior slope.

2. Information Disclosure Statement

Various instrumentation and methods have been heretofore developed for preparing the proximal end of a tibia to receive a proximal tibial prosthesis. Whiteside, U.S. Pat. No. 4,467,801, issued Aug. 28, 1984, discloses instrumentation and methods which uses the long central axis of a tibia as a guide in preparing the proximal end of the tibia to receive a proximal tibia prosthesis. The Whiteside U.S. Pat. No. 4,467,801 teaches shaping of the proximal tibial surface by first using an oscillating saw to resect a small amount of the superior proximal surface to form an approximately planar surface. A combination reamer/alignment guide is then advanced through the approximate location on the superior proxima surface of the tibia which corresponds to the central long axis of the tibia to form an intramedullary hole or bore down the center of the tibial shaft into the medullary canal of the tibia. The reamer/alignment guide has a longitudinal axis that will be aligned with the longitudinal or long axis of the tibia shaft once the reamer/alignment guide is fully inserted into the tibia. After the reamer/alignment guide is fully inserted into the tibia, a plateau planer is attached to the upper end thereof in such a manner that the cutting surfaces of the planer is transverse to the longitudinal axis of the reamer/alignment guide and, therefore, to the longitudinal or long axis of the tibia.

Nothing in the known prior art discloses or suggests the present invention. More specifically, nothing in the known prior art discloses or suggests instrumentation or a method including an intramedullary alignment guide for engaging the tibia, and a rotational alignment guide means for guiding the insertion of a rod portion of the intramedullary alignment guide into an intramedullary bore in the tibia with the intramedullary alignment guide rotationally aligned with the intramedullary bore so that the longitudinal axis of a handle portion of the intramedullary alignment guide is angled posteriorly with respect to the longitudinal axis of the rod portion and the longitudinal axis of the intramedullary bore as the rod portion of the intramedullary alignment guide is inserted into the intramedullary bore.

SUMMARY OF THE INVENTION

The present invention allows a surgeon to accurately prepare the tibial plateau surface with a posterior slope for total knee replacement. After the tibial canal is properly reamed, an intramedullary alignment guide rod is inserted into the prepared canal. The portion of the alignment guide rod that extends from the tibial bone is angled posteriorly, and a cutting means is attached thereto in order to achieve the posteriorly sloped cut on the tibial surface. The rotational stability of the intramedullary alignment guide rod is controlled by protrusions or fins that extend from the rod and which engage the proximal tibial bone ensuring a precisely prepared bone surface.

The instrumentation of the present invention includes, in general, an intramedullary alignment guide means for engaging a tibia; the intramedullary alignment guide means including an elongated rod portion having a longitudinal axis, a first end, and a second end for inserting into the intramedullary bore of the tibia with the longitudinal axis of the rod portion substantially aligned with the longitudinal axis of the intramedullary bore; and a handle portion having a first end, a second end, and a longitudinal axis extending between the first and second ends thereof with the second end of the handle portion attached to the first end of the rod portion such that the longitudinal axis of the handle portion is angled posteriorly with respect to the longitudinal axis of the rod portion and to the longitudinal axis of the intramedullary bore of the tibia when the rod portion is properly positioned in the intramedullary bore; and rotational alignment guide means for attachment to the intramedullary alignment guide means and for providing a guide for the insertion of the second end of the rod portion of the intramedullary alignment guide means into the intramedullary bore of the tibia with the intramedullary alignment guide means rotationally aligned with the tibia so that the longitudinal axis of the handle portion is angled posteriorly with respect to the longitudinal axis of the rod portion and the longitudinal axis of the intramedullary bore of the tibia.

BRIEF DESCRIPTION OF THE DRAWINGS

FIG. 11 is top plan view of an alignment pin holder of a rotational alignment guide means of the intramedullary instrumentation of the present invention.

FIG. 12 is a sectional view substantially as taken on line 12—12 of FIG. 11 on a somewhat enlarged scale.

FIG. 13 is a side elevation view of the alignment pin holder of FIG. 12 with portions thereof broken away.

FIG. 14 is a sectional view similar to FIG. 12 but showing the alignment pin holder in combination with the intramedullary alignment guide of FIGS. 1-5.

FIG. 15 is a sectional view similar to FIG. 7 but showing an intramedullary alignment guide being inserted into the intramedullary bore in the tibial in combination with an alignment pin, an alignment pin holder, and a driver cap.

FIG. 16 is similar to FIG. 15 but shows the intramedullary alignment guide fully inserted into the intramedullary bore in the tibia.

DESCRIPTION OF THE PREFERRED EMBODIMENT

Figure 9:
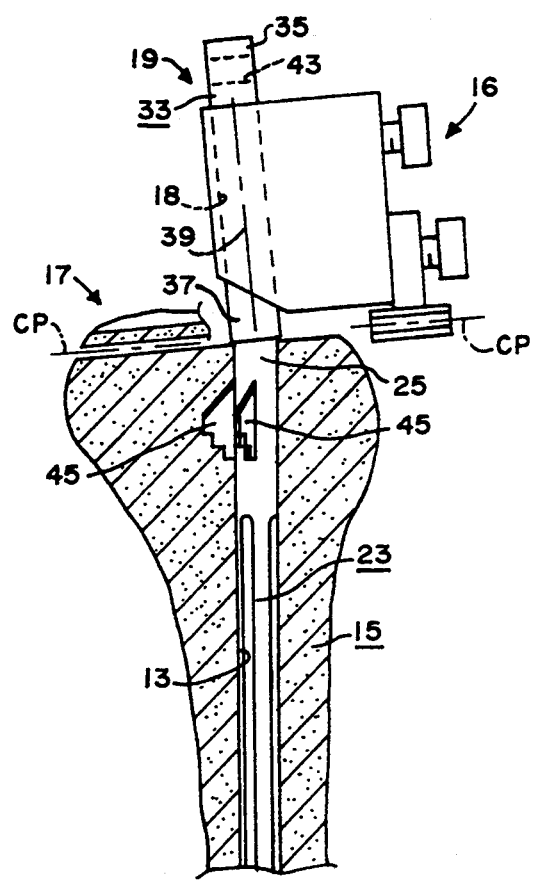
FIG. 9 is a view similar to FIG. 8 but showing a cutting means attached to the intramedullary alignment guide.

The intramedullary instrumentation 11 of the present invention uses an intramedullary bore 13 formed in the proximal end of a tibia 15 as a reference to accurately position a cutting means 16 relative to the proximal end, or tibial plateau surface, 17 of the tibia 15 for allowing a surgeon to prepare the tibial plateau surface 17 with a posterior slope. The cutting means 16 may include of a plateau planer such as the plateau planer 30 disclosed by Whiteside, U.S. Pat. No. 4,467,801, issued Aug. 28, 1984, incorporated herein by reference, may include a typical cutting guide block such as the cutting guide block 70 disclosed by Whiteside et al., U.S. Pat. No. 5,002,545, issued Mar. 26, 1991, incorporated herein by reference, for guiding a conventional resection tool such as an oscillating saw or a hand saw, or may include various other cut guides now apparent to those skilled in the art. The cutting means 16 shown in FIG. 9 is representative of a typical cutting guide block such as disclosed in the U.S. Pat. No. 5,002,545 and has an opening or bore 18 that is perpendicular to the cutting plane CP thereof.

The intramedullary instrumentation 11 includes, in general, an intramedullary alignment guide means 19 for engaging the tibia 15, and rotational alignment guide means 21 for use in accurately positioning the intramedullary alignment guide means 19 relative to the tibia 15. The intramedullary alignment guide means 19 and the rotational alignment guide means 21 are shown in combination in FIGS. 15 and 16.

The intramedullary alignment guide means 19 includes an elongated lower end or rod portion 23 having a first or proximal end 25, a second or distal end 27, and a longitudinal axis 29 extending between the first and second ends 25, 27. In use, the second end 27 of the rod portion 23 is inserted into the intramedullary bore 13 of the tibia 15 with the longitudinal axis 29 of the rod portion 23 aligned or substantially aligned with the longitudinal axis 31 of the proximal end of the tibia 15.

Figure 1:
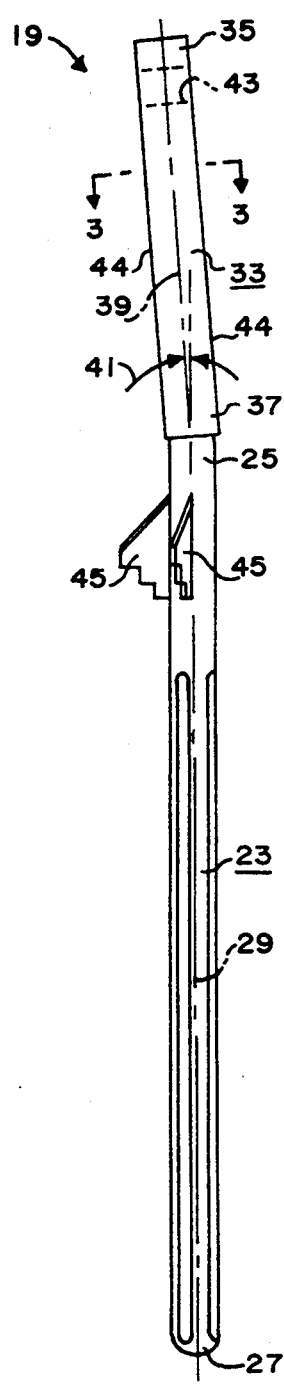
FIG. 1 is a side elevation view of an intramedullary alignment guide of the intramedullary instrumentation of the present invention.
Figure 2:
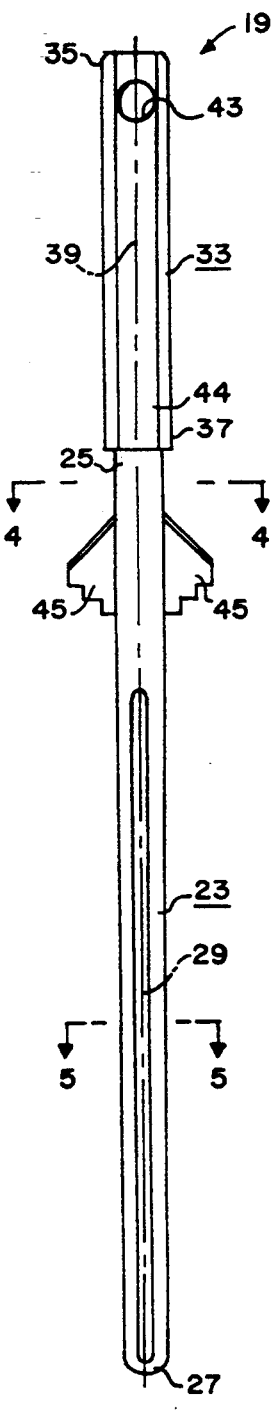
FIG. 2 is a front elevation view of the intramedullary alignment guide of FIG. 1.
Figure 3:
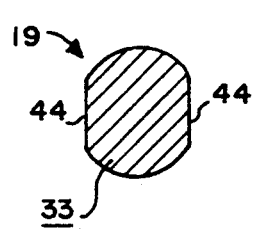
FIG. 3 is a sectional view substantially as taken on line 3—3 of FIG. 1 with portions omitted for clarity and on a somewhat enlarged scale.
Figure 4:
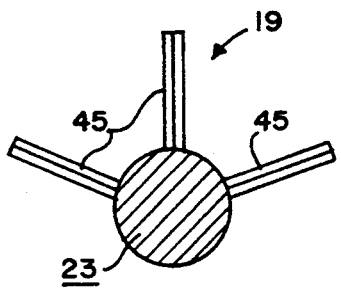
FIG. 4 is a sectional view substantially as taken on line 4—4 of FIG. 2 on a somewhat enlarged scale.
Figure 5:
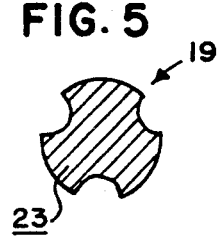
FIG. 5 is a sectional view substantially as taken on line 5—5 of FIG. 2 on a somewhat enlarged scale.
Figure 6:
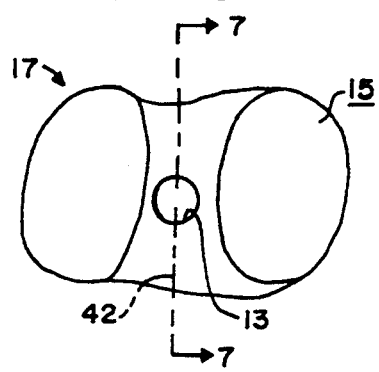
FIG. 6 is a top plan view of a human tibia having a intramedullary bore formed therein substantially parallel to the long axis thereof for receiving the intramedullary alignment guide of FIGS. 1-5.
Figure 7:
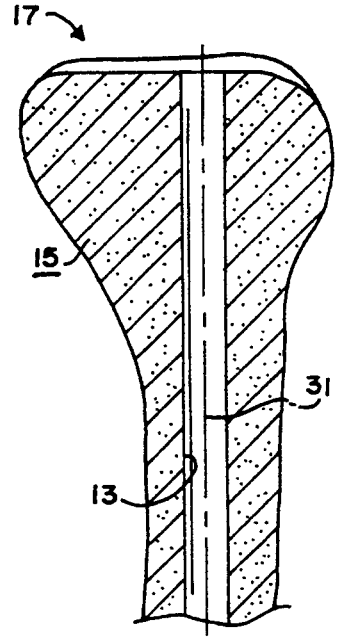
FIG. 7 is a sectional view substantially as taken on line 7—7 of FIG. 6.
Figure 8:
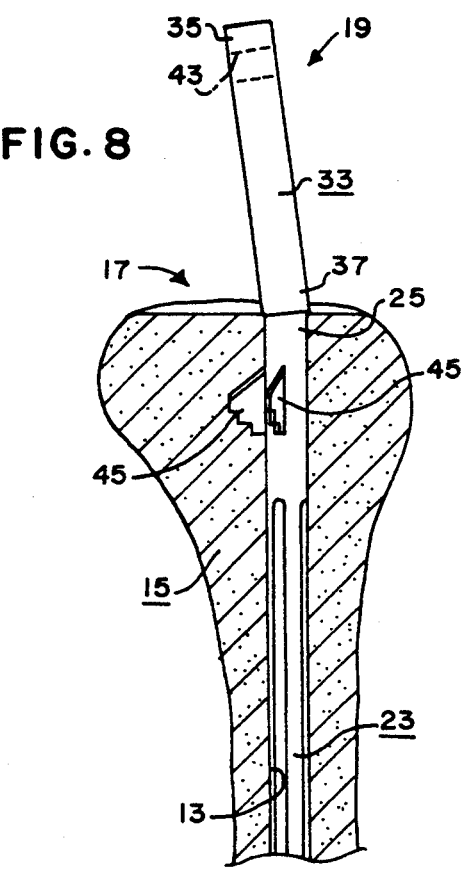
FIG. 8 is a sectional view similar to FIG. 7 but showing the intramedullary alignment guide of FIGS. 1-5 inserted into the intramedullary bore in the tibia.
Figure 10:
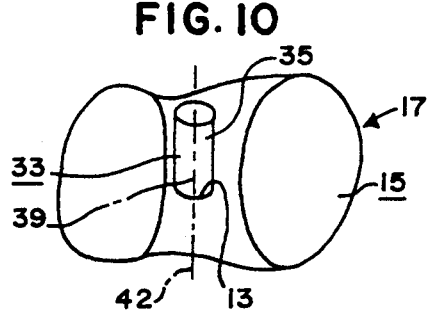
FIG. 10 is a top plan view of a human tibia similar to FIG. 6 but with the intramedullary alignment guide fully inserted into the intramedullary bore in the tibia, showing the intramedullary alignment guide properly rotationally aligned with the tibia plateau.

The intramedullary alignment guide means 19 includes an upper end or handle portion 33 having a first or proximal end 35, a second or distal end 37, and a longitudinal axis 39 extending between the first and second ends 35, 37. The second end 37 of the handle portion 33 is attached to the first end 25 of the rod portion 23 with the longitudinal axis 39 of the handle portion 33 set at a pre-selected angle 41 (see FIG. 1) with respect to the longitudinal axis 29 of the rod portion 23. The angle 41 preferably corresponds to the desired posterior slope of a tibial plateau surface for use with a total knee replacement and may be, for example, 5° or so. In use, when the rod portion 23 is properly inserted into the intramedullary bore 13 of the tibia 15, the longitudinal axis 39 of the handle portion 33 will be parallel with the sagittal plane 42 of the tibia 15 (see FIGS. 6 and 10). A circular bore or aperture 43 is preferably provided through the handle portion 33 transverse to the longitudinal axis 39 and extending between the anterior and posterior sides of the handle portion 33 substantially adjacent the first end 35. Opposite sides of the handle portion 33 preferably have flat areas 44 in order to allow the cutting guide 16 to be mounted thereon in a nonrotatable manner.

The intramedullary alignment guide means 19 preferably has a series of spaced protrusions or fins 45 extending from the outer surface of the rod portion 23 just distally of the first end 25 thereof.

The intramedullary alignment guide means 19 may be constructed in various manners, out of various materials and in various sizes as will now be apparent to those skilled in the art. Preferably, the intramedullary alignment guide means 19 is constructed in the manner and out of the material taught by Whiteside et al, U.S. Pat. No. 5,002,545, issued Mar. 26, 1991, incorporated herein by reference, relative to the intramedullary alignment guide 10 thereof with the exception that the angle 41 of the intramedullary alignment guide means 19 of the present invention is preferably about 5° as hereinabove stated rather than between about 9° and 12° as taught by the U.S. Pat. No. 5,002,545.

The rotational alignment guide means 21 preferably includes means such as an elongated alignment pin 47 having a longitudinal axis 49 for attachment to the intramedullary alignment guide means 19 with the longitudinal axis 49 thereof parallel with the longitudinal axis 29 of the rod portion 23 of the intramedullary alignment guide means 19 and for providing a visual or tactile guide to insure that the intramedullary alignment guide means 19 is rotationally aligned with the tibial plateau surface 17 as the second end 27 of the rod portion 23 is inserted into the intramedullary bore 13 in the tibia 15.

The rotational alignment guide means 21 preferably includes attachment means 51 for attaching the alignment pin 47 to the handle portion 33 of the intramedullary alignment guide means 19 with the longitudinal axis 49 of the alignment pin 47 parallel with the longitudinal axis 29 of the rod portion 23 of the intramedullary alignment guide means 19. The attachment means 51 preferably includes an alignment pin holder 53 having a first end 55 for attachment to the handle portion 33 of the intramedullary alignment guide means 19, having a second end 57 for attachment to the alignment pin 47, and having a longitudinal axis 59 extending between the first and second ends 55, 57. The first end 55 of the alignment pin holder 53 is preferably adapted to extend through the aperture 43 through the first end 35 of the handle portion 33 of the intramedullary alignment guide means 19. The second end 57 of the alignment pin holder 53 preferably has an aperture 61 therethrough for receiving the alignment pin 47. The aperture 61 is preferably angled relative to the longitudinal axis 59 of the alignment pin holder 53 an amount proportional to the angle 41 between the longitudinal axis 29 of the rod portion 23 and the longitudinal axis 39 of the handle portion 33 of the intramedullary alignment guide means 19. More specifically, the angle 63 between the longitudinal axis 65 of the aperture 61 and a plane 65 that is perpendicular to the longitudinal axis 59 of the alignment pin holder 53 as shown in FIG. 13 is preferably the same as the angle 41 between the longitudinal axis 29 of the rod portion 23 and the longitudinal axis 39 of the handle portion 33 of the intramedullary alignment guide means 19. A thumb screw 69 or the like is preferably provided for coacting with a threaded aperture 71 in the alignment pin holder 53 opening into the aperture 61 for fixedly securing the alignment pin 47 to the alignment pin holder 53 as will now be apparent to those skilled in the art.

The rotational alignment guide means 21 may be constructed in various manners, out of various materials, and in various sizes as will now be apparent to those skilled in the art. For example, the various components of the rotational alignment guide means 21 may be machined or otherwise formed out of surgical grade stainless steel or the like in sizes corresponding to the intramedullary alignment guide means 19, etc.

The intramedullary instrumentation 11 preferably includes positioning means for insuring that the alignment pin holder 53 is properly positioned relative to the handle portion 33 of the intramedullary alignment guide means 19 and for insuring that the longitudinal axis 63 of the aperture 61 through the alignment pin holder 53 is parallel with the longitudinal axis 29 of the rod portion 23 of the intramedullary alignment guide means 19 when the alignment pin holder 53 is attached to the handle portion 33 and the alignment pin 47 is attached to the alignment pin holder 53. The positioning means may include a longitudinal groove 73 in the first end 55 of the alignment pin holder 53, a key 75 in the aperture 43 through the handle portion 33, and a shoulder 77 on the alignment pin holder 53 between the first and second ends 55, 57 thereof.

In the preferred method of using the intramedullary instrumentation 11, the intramedullary bore 13 is first formed in the tibia 15 in any known manner. For example, the knee may be hyerflexed, the tibial spines removed with an oscillating saw to the level of the highest tibial articular surface, and an intramedullary reamer inserted into the center of the cancellous surface produced by removing the tibial spines and alternately tapped and turned until it is well-seated in the medullary canal of the tibia 15, thereby forming the intramedullary bore 13 as will now be apparent to those skilled in the art. The intramedullary reamer is then removed from the tibia 15. The elongated alignment pin 47 of the rotational alignment guide means 21 is attached to the intramedullary alignment guide means 19 via the alignment pin holder 53. That is, the first end 55 of the alignment pin holder 53 is inserted into the aperture 43 through the handle portion 33 of the intramedullary alignment guide means 19 and the elongated alignment pin 47 is inserted into the aperture 61 through the second end 57 of the alignment pin holder 53 and secured to the alignment pin holder 53 by the thumb screw 69 or the like. The positioning means (e.g., the longitudinal groove 73 in the first end 55 of the alignment pin holder 53 and the key 75 in the aperture 43 through the handle portion 33 of the intramedullary alignment guide means 19) insures that the longitudinal axis 49 of the elongated alignment pin 47 is parallel with the longitudinal axis 29 of the rod portion 23 of the intramedullary alignment guide means 19, and that the longitudinal axis 49 of the elongated alignment pin 47 and the longitudinal axes 29, 39 of the rod portion 23 and handle portion 33, respectively, of the intramedullary alignment guide means 19 are in a single plane. The second end 27 of the rod portion 23 is then inserted into the intramedullary bore 13. A cap 79 may be placed over the first end 35 of the handle portion 33 of the intramedullary alignment guide 19 to allow a mallet or the like to be used to drive the rod portion 23 of the intramedullary alignment guide 19 into the intramedullary bore 13 as will now be apparent to those skilled in the art. As the rod portion 23 is driven into the intramedullary bore 13, the surgeon uses the elongated alignment pin 47 as a visual and tactile guide to insure that the rod portion 23 is being properly inserted into the intramedullary bore 13 with the rod portion 23 rotationally aligned with the tibia plateau 17 so that the longitudinal axis 39 of the handle portion 33 is parallel to the sagittal plane 42 of the tibial 15 and is angled exactly posteriorly with respect to the longitudinal axis 29 of the rod portion 23 and the longitudinal axis 31 of the tibia 15. After the rod portion 23 is fully inserted into the intramedullary bore 13, with the fins 45 engaging portions of the tibia 15, the cap 79 and alignment pin holder 53 are removed from the handle portion 33 of the intramedullary alignment guide means 19. A cutting means 16 can then be inserted onto the handle portion 33 by inserting the bore 18 thereof over the first end 35 of the handle portion 33 of the intramedullary alignment guide means 19. The cutting means 16 can then be used in the typical manner to shape the tibial plateau 17. However, use of the intramedullary instrumentation 11 of the present invention will insure that the cut produced by the cutting means 16 will have a posterior slope based on the angle 41 and that such posterior slope will be properly rotational aligned with the tibia 15.

Although the present invention has been described and illustrated with respect to a preferred embodiment and a preferred use therefor, it is not to be so limited since modifications and changes can be made therein which are within the full intended scope of the invention.

We claim:

1. Instrumentation for use with a tibia having a tibial plateau surface and an intramedullary bore having a longitudinal axis extending from the tibia plateau surface and for positioning means for preparing the tibial plateau surface with a posterior slope; said instrumentation comprising:
   a) an intramedullary alignment guide means for engaging a tibia; said intramedullary alignment guide means including:
      (i) an elongated rod portion having a longitudinal axis, a first end, and a second end for inserting into the intramedullary bore of the tibia with said longitudinal axis of said rod portion substantially aligned with the longitudinal axis of the intramedullary bore;
      (ii) a handle portion having a first end, a second end, and a longitudinal axis extending between said first and second ends thereof with said second end of said handle portion attached to said first end of said rod portion such that said longitudinal axis of said handle portion is angled posteriorly with respect to said longitudinal axis of said rod portion and to the longitudinal axis of the intramedullary bore of the tibia when said rod portion is properly positioned in the intramedullary bore;
   b) rotational alignment guide means for attachment to said intramedullary alignment guide means and for providing a guide for the insertion of said second end of said rod portion of said intramedullary alignment guide means into the intramedullary bore of the tibia with said intramedullary alignment guide means rotationally aligned with the tibia so that said longitudinal axis of said handle portion is angled posteriorly with respect to said longitudinal axis of said rod portion and the longitudinal axis of the intramedullary bore of the tibia; said rotational alignment guide means including:
  (i) an elongated alignment pin means having a longitudinal axis for attachment to said intramedullary alignment guide means with said longitudinal axis of said alignment pin parallel to said longitudinal axis of said rod portion of said intramedullary alignment guide means and for providing a visual guide that said intramedullary alignment guide means is rotationally aligned with the intramedullary bore in the tibia as said second end of said rod portion of said intramedullary alignment guide means is inserted into the intramedullary bore; and
  (ii) attachment means for attaching said alignment pin means to said handle portion of said intramedullary alignment guide means with said longitudinal axis of said alignment pin means parallel to said longitudinal axis of said rod portion of said intramedullary alignment guide means; said attachment means of said rotational alignment guide means including an alignment pin holder having a first end for attachment to said handle portion of said intramedullary alignment guide means and having a second end for attachment to said alignment pin means; and
c) positioning means for insuring that said alignment pin holder is properly positioned relative to said intramedullary alignment guide means and for insuring that said longitudinal axis of said alignment pin means is positioned parallel to said longitudinal axis of said rod portion of said intramedullary alignment guide means; said positioning means including a non-circular end on said alignment pin holder of said attachment means of said rotational alignment guide means and non-circular aperture means through said intramedullary alignment guide means for receiving said non-circular end on said alignment pin holder; the cross sections of said non-circular end on said alignment pin holder and said non-circular aperture means through said intramedullary alignment guide means are substantially identical in size and shape so that said alignment pin holder will be properly positioned relative to said intramedullary alignment guide means and said longitudinal axis of said alignment pin means will be positioned parallel to said longitudinal axis of said rod portion of said intramedullary alignment guide means when said non-circular end on said alignment pin holder is received in said non-circular aperture means through said intramedullary alignment guide means.

2. Instrumentation for use with a tibia having a tibial plateau surface and an intramedullary bore having a longitudinal axis extending from the tibia plateau surface and for positioning means for preparing the tibial plateau surface with a posterior slope; said instrumentation comprising, in combination:
  a) an intramedullary alignment guide means for engaging a tibia; said intramedullary alignment guide means including:
    (i) an elongated rod portion having a longitudinal axis, a first end, and a second end for inserting into the intramedullary bore of the tibia with said longitudinal axis of said rod portion substantially aligned with the longitudinal axis of the intramedullary bore;
    (ii) a handle portion having a first end, a second end, and a longitudinal axis extending between said first and second ends thereof with said second end of said handle portion attached to said first end of said rod portion such that said longitudinal axis of said handle portion is angled posteriorly with respect to said longitudinal axis of said rod portion and to the longitudinal axis of the intramedullary bore of the tibia when said rod portion is properly positioned in the intramedullary bore; said first end of said handle portion of said intramedullary alignment guide means having an aperture therethrough;
  b) rotational alignment guide means attached to said intramedullary alignment guide means and for providing a guide for the insertion of said second end of said rod portion of said intramedullary alignment guide means into the intramedullary bore of the tibia with said intramedullary alignment guide means rotationally aligned with the tibia so that said longitudinal axis of said handle portion is angled posteriorly with respect to said longitudinal axis of said rod portion and the longitudinal axis of the intramedullary bore of the tibia; said rotational alignment guide means including:
    (i) an elongated alignment pin means having a longitudinal axis attached to said intramedullary alignment guide means with said longitudinal axis of said alignment pin parallel to said longitudinal axis of said rod portion of said intramedullary alignment guide means and for providing a visual guide that said intramedullary alignment guide means is rotationally aligned with the intramedullary bore in the tibia as said second end of said rod portion of said intramedullary alignment guide means is inserted into the intramedullary bore; and
    (ii) attachment means attaching said alignment pin means to said handle portion of said intramedullary alignment guide means with said longitudinal axis of said alignment pin means parallel to said longitudinal axis of said rod portion of said intramedullary alignment guide means; said attachment means of said rotational alignment guide means including an alignment pin holder having a first end attached to said handle portion of said intramedullary alignment guide means and received in said aperture through said first end of said handle portion of said intramedullary alignment guide means and having a second end for attachment to said alignment pin means; said second end of said alignment pin holder having an aperture therethrough receiving said alignment pin means of said rotational alignment guide means, said aperture through said second end of said alignment pin holder having a longitudinal axis parallel to said longitudinal axis of said rod portion of said intramedullary alignment guide means when said first end of said alignment pin holder is properly positioned in said aperture through said first end of said handle portion of said intramedullary alignment guide means; and
  c) positioning means for insuring that said first end of said alignment pin holder is properly positioned in said aperture through said first end of said handle portion of said intramedullary alignment guide means and for insuring that said longitudinal axis of said aperture through said second end of said alignment pin holder parallel to said longitudinal axis of said rod portion of said intramedullary alignment guide means: said positioning means including a longitudinal groove in said first end of said alignment pin holder, and a key in said aperture through said handle portion of said intramedullary alignment guide means received in said longitudinal groove in said first end of said alignment pin holder; the cross sections of said longitudinal groove in said first end of said alignment pin holder and said key in said aperture through said handle portion of said intramedullary alignment guide means are substantially identical in size and shape so that said alignment pin holder will be properly positioned relative to said intramedullary alignment guide means and said longitudinal axis of said alignment pin means will be positioned parallel to said longitudinal axis of said rod portion of said intramedullary alignment guide means when said first end of said alignment pin holder is received in said aperture through said handle portion of said intramedullary alignment guide means.

* * * * *